US012674743B1

(12) United States Patent
McDonnell et al.

(10) Patent No.: US 12,674,743 B1
(45) **Date of Patent: *Jul. 7, 2026**

(54) HAMMER ACTIVATED MEASUREMENT SYSTEM FOR TESTING AND EVALUATING RUBBER AND OTHER MATERIALS

(71) Applicant: The United States of America, as represented by the Secretary of the Navy, Arlington, VA (US)

(72) Inventors: James McDonnell, West Chester, PA (US); Lisa Weiser, Cherry Hill, NJ (US); Jaime Santiago, Annapolis, MD (US); Colin Ratcliffe, Millersville, MD (US)

(73) Assignee: The United States of America, as represented by the Secretary of the Navy, Arlington, VA (US)

( * ) Notice: Subject to any disclaimer, the term of this patent is extended or adjusted under 35 U.S.C. 154(b) by 479 days.

This patent is subject to a terminal disclaimer.

(21) Appl. No.: 18/457,597

(22) Filed: Aug. 29, 2023

Related U.S. Application Data

(63) Continuation-in-part of application No. 16/731,759, filed on Dec. 31, 2019, now Pat. No. 11,781,967.

(60) Provisional application No. 62/844,509, filed on May 7, 2019.

(51) Int. Cl.
| | |
|---|---|
| *G01N 19/04* | (2006.01) |
| *G01N 29/04* | (2006.01) |
| *G01N 29/44* | (2006.01) |
| *G01N 33/208* | (2019.01) |
| *G01N 33/00* | (2006.01) |

(52) U.S. Cl.
CPC ........... *G01N 19/04* (2013.01); *G01N 29/045* (2013.01); *G01N 29/4418* (2013.01); *G01N*

*33/208* (2019.01); *G01N 33/0083* (2024.05); *G01N 2291/0231* (2013.01)

(58) Field of Classification Search
CPC ...... G01N 19/00; G01N 19/04; G01N 33/208; G01N 29/045; G01N 29/4418
USPC ........................................................ 114/342
See application file for complete search history.

(56) References Cited

U.S. PATENT DOCUMENTS

| | | | |
|---|---|---|---|
| 4,479,386 A | 10/1984 | Beggs et al. | |
| 4,567,764 A | 2/1986 | Jamison et al. | |
| 5,526,689 A | 6/1996 | Coulter et al. | |
| 6,339,958 B1 | 1/2002 | Tsui et al. | |
| 6,748,791 B1 | 6/2004 | Georgeson et al. | |
| 11,781,967 B1 * | 10/2023 | McDonnell ............ | G01N 19/04 |
| | | | 114/342 |

(Continued)

FOREIGN PATENT DOCUMENTS

CN          102353700 B          2/2012

OTHER PUBLICATIONS

U.S. Department of the Navy; 2016 Navy ManTech Project Book at p. 101; Modified SHT Debond Detector to Save Costs on In-Service VCS Hull; Office of Naval Research (2016); available at https://nsam.ati.org/wp-content/uploads/2016/09/2016_ProjectBook.pdf.

*Primary Examiner* — Lars A Olson
(74) *Attorney, Agent, or Firm* — Mark J. Rosen; Naval Surface Warfare Center, Philadelphia Division

(57) ABSTRACT

Devices and methods are provided for determining whether a laminate structure is in a bonded or debonded state. The devices and methods provide simple, accurate, rapid, cost-effective, and reliable means for assessing the bonding state of such laminated structures.

20 Claims, 6 Drawing Sheets

(56) References Cited

U.S. PATENT DOCUMENTS

| | | |
|---|---|---|
| 2012/0131702 A1 | 5/2012 | Shi et al. |
| 2017/0307500 A1 | 10/2017 | Girrell et al. |

* cited by examiner

HAMMER ACTIVATED MEASUREMENT SYSTEM FOR TESTING AND EVALUATING RUBBER AND OTHER MATERIALS

STATEMENT OF GOVERNMENT INTEREST

The invention described herein may be manufactured and used by or for the Government of the United States of America for governmental purposes without payment of any royalties thereon or therefor.

FIELD OF THE INVENTION

The invention is related to the field of adhesion of layers in a laminate structure, particularly to a method and device for quickly and easily determining whether such layers in a laminate are well bonded.

BACKGROUND OF THE INVENTION

The metal hulls of ocean-going vessels are generally equipped with outer coatings or plating to accomplish a variety of purposes. These purposes include protecting the metal hull from the corrosive effect of seawater, providing resistance to biological growth on the surface of the hull, reducing friction, improving fuel efficiency, and other goals. The metal hulls of submarines are generally equipped with a laminate hull treatment, an outer plating to confer additional advantages, including providing the hull with a less actively reflective acoustic signature. Such anechoic coatings or platings accomplish several goals, including reducing the sounds emanating from within the submarine and from its motion through water, and provide other advantageous acoustic and hydrodynamic properties.

These and other purposes may be achieved by bonding or otherwise adhering to the hull's surface an exterior hull coating (EHC) whose material composition is adapted for such purposes. EHC may be composed of a variety of materials, as further described herein.

EHC may be bonded to the hull surface of a submarine in discrete individual tiles, using an appropriate marine-worthy adhesive. Alternatively, EHC may be molded in place in large segments and likewise adhered to the hull using such an adhesive. Over the course of a submarine's life, the EHC bonded to the hull may loosen in particular sections, becoming detached (i.e., debonded or delaminated) from the hull. Such debonding reduces the effectiveness of the EHC in deadening the submarine's acoustic signature. Additionally, while some regions suffering from complete debonding of EHC may be visually observable, other regions of debonding may be completely invisible to the naked eye. Both complete and incomplete debonding reduce the effectiveness of EHC.

Where debonding has occurred, one preferred corrective measure is to fully remove and replace the loosened sections with replacement EHC, generally in the form of new tiles. Determining which regions of EHC have become partially detached is a difficult process fraught with problems of both overdetection (e.g., identifying EHC regions as debonded which are not in fact debonded) and underdetection (e.g., identifying EHC regions as bonded which are in fact debonded). Ideally, the detection process is performed non-destructively such that well-bonded tiles are neither destroyed nor damaged during detection.

Early efforts to detect EHC debonding from submarine hulls relied on manual inspection, both visual and by tapping the EHC, but such methods are highly prone to inaccuracy, yielding both overdetection and underdetection. Technicians may hand-tap the hull with a simple tool such as a putty knife, to listen for strange sounds which may indicate a debonded area. The effectiveness of such manual detection is limited by an individual's hearing ability and surrounding noise in the area. Ports, docks, and dry-docks where such detection usually takes place tend to be particularly loud environments. As such, manual detection is highly subjective, and prone to error.

NASA struggled with a similar problem detecting the detachment of foam insulation from rocket engines. U.S. Pat. No. 4,479,386 describes one solution for non-destructive testing of foam insulation in which a force-measuring hammer is wielded to strike a location of the insulation, measuring the force of the impact and the resulting force vibration, which after a fast Fourier transform produces an energy spectral density curve. The frequency where the curve terminates is compared to a predetermined empirical scale, allowing one to determine the degree of debonding at the point of impact. The predetermined empirical scale is highly dependent on the characteristics of the foam coating and the surfaces of the rockets to which it is adhered.

For such mechanical testing, the general approach to identifying structural dynamic properties is to excite the target structure, then measure the response of the structure. Various transfer functions between the input and output can then be determined by relating the response to the excitation. For a dynamically well-behaved structure, variations from a footprint transfer function can be used to identify changes which might indicate a debonded state. The transfer functions are often processed in the frequency domain, as with the method described in the '386 Patent, examining the frequency reactions of the substrate after an impact.

The Navy developed a device known as the Thumper for detection of EHC debonding using an impulse hammer applying a similar analysis in the frequency domain. See 2016 Navy ManTech Project Book at p. 101, incorporated herein by reference. While the device yields more accurate results than manual inspection, it is still prone to both overdetection and underdetection. The tool employs a solenoid to hit the hull and the tool was equipped with multiple accelerometers to measure the response of the EHC to the impact. While this system may be an improvement over hand tapping, the method was limited because of its sensitivity to orientation, temperature, and battery power. These sensitivities required the unit to be recalibrated frequently, making the hull survey process very slow. The unit also had to be calibrated on a section of the hull with well bonded EHC, but in view of the many suspect areas it posed challenges to finding a suitable region on which to calibrate.

It is also an unwieldy method because the impulse hammer device is relatively heavy at approximately ten pounds and requires the user to exert approximately thirty pounds of force to operate the device effectively. These disadvantages contribute to requiring long periods of time to examine an entire hull, in which approximately 30,000 measurements would ideally be made.

With the variety of materials used for laminating submarines, variations in their thickness, and variations in the hulls' thickness and properties, generating such empirical scales against which to compare the results of such force hammer's impacts, as required by the existing method, presents a challenge to the adaptability of a detection device to be used on a variety of hulls and platings throughout a fleet. For EHC, a single, consistent footprint transfer function is not easily derivable for comparison because the transfer function for a well bonded region of EHC depends on characteristics of the particular EHC materials, the thicknesses thereof, and the nature of the sections of hull to which they are adhered. Different parts of a submarine provide different mechanical support to the EHC. For example, differential hull thickness and stiffness characteristics of different sections of the hull lead to varying support and boundary conditions for the EHC. For existing detection processes, these issues would require a different baseline transfer function for comparison for each set of characteristics of EHC and hull. Even if one could derive such baselines, however, it may still be difficult to discriminate between those transfer function changes resulting from debonding as opposed to such changes resulting from other causes. The input/output approach, therefore, may lead to difficult and unreliable in-field detection of debonded EHCs.

Other methods to detect debonding have been used, including variations of visual and ultrasonic inspection. Such methods require significant portions of EHC to be removed to access the hull structure, which removed sections must later be replaced. This unnecessarily increases the cost of detection.

Other laminated structures also suffer from debonding or partial debonding. Such laminates may be composed of as few as two layers of equal or different thicknesses, sandwiches of three or more layers of varying thickness, and the like. It is desirable to be able to ascertain the degree of bonding between such layers in such laminate structures.

The art is in need of improved ways to detect insufficient bonding and partial debonding of the layers in a laminate structure without the disadvantages of current designs.

SUMMARY OF THE INVENTION

Given the aforementioned problems in the art, it is an object of the invention to provide a reliable, efficient, and easy to use device and method for shipyard personnel to use to determine whether EHC is in a bonded state or debonded state, which method and device provide for detection far more rapidly and far more accurately than existing devices and methods. The apparatuses and methods of the invention are referred to herein as the Hammer Activated Measurement System for Testing and Evaluating Rubber (HAMSTER).

The invention is equally adaptable to a variety of substrates coated with a variety of laminates to provide desirable advantageous characteristics. Exemplary substrates include the metal of a ship's hull and the metal of an aircraft's body. Other substrates may include other structurally strong materials such as carbon fiber, ceramics, woods, plastics, polymers, resins, fiberglass, glass, composites, and the like. The invention also contemplates laminate materials adhered to such substrates, such laminates including foams, ceramics, plastics, polymers, resins, rubber, and the like. The term "rubber" as used herein (and in the acronym HAMSTER) includes such laminate materials. Other laminate structures include composite structures of two layers of equal or different thicknesses, sandwiches of three or more layers of varying thickness, and the like. The thickness of such laminates may vary from thinner coatings or layers less than one quarter of an inch thick to thicker coatings or layers greater than four inches thick.

Thus, while the term "substrate" generally suggests a laminate structure typically having a thicker layer on which a thinner coating layer is applied, the term "substrate" as used herein may describe any of the layers in a layered laminate structure, whether thicker or thinner than its adjacent layers. Accordingly, "substrate-laminates" and "substrate-laminate structures" as used herein refer to any laminate structures having at least two layers. The devices and methods of the invention contemplate assessing debonding in a wide variety of such laminate structures. For example, typical substrate-laminate structures include such laminate structures as EHC applied to metal hulls. Others include laminates used for armor, such as body armor, ballistic tile, helicopter blade composites, layered fiberglass and fiberglass sandwiches, layered carbon fiber, and numerous other layered laminate structures.

While HAMSTER is equally adaptable for a wide range of layered laminates and thicknesses, it is also particularly adept at detecting debonding or delaminating of EHC from ships' hulls. HAMSTER is useful in the more general art of detecting the state of bonding between layers in a laminate structure.

Well-bonded substrate-laminate structures, whether they be hull-EHC or other combinations of materials, behave predominantly as linear single degree of freedom mass/spring/damper mechanical systems. However, when the laminate is even partially debonded from the substrate the system is no longer amenable to analysis with such a mathematical model. The instant invention provides for a method of identifying such noncompliance and thus permits the detection of debonded regions. Moreover, the methods and devices of the invention provide rapid results with high accuracy in such detection.

According to the invention, rather than calculating input/output transfer functions in the frequency domain, the HAMSTER measures only the excitation force pulse during impact, and the calculations are performed in the time domain. The force versus time measurements data, that is, pulse curves, may be represented graphically as pulse impulse traces. These resulting pulse curves are then normalized (in time and total impulse) to remove the effects of material differences and structural support stiffness differences. The normalized pulse curve data can then be compared with that of a universal profile representing the pulse characteristics of well-bonded laminate.

The universal profile may be constructed by using a larger number of sample impulse data. Each normalized pulse from these samples can be described parametrically by being subjected to a mathematical regression to ascertain parameters which mathematically describe the pulse curves. Averaging a sufficient number of measurements enables construction of a universal profile pulse curve defined mathematically by such parameters. The profile thus represents the post-normalization pulse curve expected for well bonded regions. With the profile determined, new impacts are examined and their resultant pulse curves are compared to the profile. Depending on the level of confidence desired, a threshold deviation from the profile is calculated using a statistical outlier process. Based on the Root Mean Square Difference (RMSD) between a sample pulse curve and the profile pulse curve, the profile threshold enables identification of those pulses which do not conform to the profile. Deviations from the profile above the threshold indicate a potential debond. Unlike other systems for detecting delamination, HAMSTER does not need data from a response transducer, nor does it require Fourier transformation of data. HAMSTER relies only on force data collected during the impact time frame.

In its simplest form, the device of the invention employs a small, handheld instrumented impulse hammer to strike regions of substrate-laminate, such as hull-EHC. The hammer is equipped with a force gauge or sensor, and a microprocessor records the force measured over a short span of time. The force sensor may alternatively be an accelerometer which outputs measured acceleration. Given that force equals the product of mass and acceleration (F=ma), force is simply calculated by multiplying the measured acceleration times the mass. Thus the force sensor outputs either a measured force, or a measured acceleration which may then be converted to force by applying F=ma. As used herein, the force may refer to a directly measured force, or an indirectly measured force calculated from a measured acceleration.

The hammer does not measure or need to measure the frequency response of the impacted material itself because, unlike other methods, the invention solely relies on the measured excitation forces during impact. This significantly reduces the complexity of the equipment and leads to simplified, faster, and more reliable detection. Such a handheld HAMSTER device provides many advantages for use. It is light in weight, accommodates a range of forces when wielded by a user, has a long battery life, provides rapid notification of bonded vs. debonded state, and requires little training for accurate and repeatable use.

In more complex forms of HAMSTER devices, the impulse hammer may be larger, mounted, automated, and/or robotically controlled. Further, a plurality of such devices may be mounted in an array formation for essentially simultaneous measuring over a larger area of laminated substrate. Such an array may be mounted on a crawler enabled to move to different locations for measuring.

In one aspect, the invention is directed to a device for detecting a bonded state or a debonded state between a substrate and a laminate, wherein the device has an impulse hammer with a hammer head having a force sensor, and a computer having programmed therein a universal profile and a threshold, such that when the impulse hammer is swung and impacts a region of the laminate for a time period, the force sensor measures force-versus-time pulse data and delivers the pulse data having a plurality of data points spanning fractions of the time period to the computer. The computer processes the pulse data by normalizing with respect to time and total pulse to form a normalized pulse curve, compares the normalized pulse curve to the universal profile, and calculates an root means square difference (RMSD) between the normalized pulse curve and the universal profile. If a pulse's RMSD exceeds the profile threshold, the computer provides a notification of a debonded state. In some aspects, the computer provides notification of a bonded state as well.

In some aspects, the impulse hammer of the invention is attached by a cord to an enclosure housing the computer. In some aspects, the device also has a battery pack and a signal conditioner housed within the enclosure, and in some aspects the enclosure has means for being worn by an operator. In other aspects, the impulse hammer itself houses the computer, a battery pack, and a signal conditioner. In another aspect, the impulse hammer communicates wirelessly with the computer.

In some aspects of the invention, the laminate structure is a substrate-laminate having two layers, such as a submarine hull, a surface ship hull, or an aircraft body, having a coating such as Exterior Hull Coating. The impulse hammer may be handheld and may weigh less than three pounds. In some aspects, the force sensor directly measures force and outputs force data. In other aspects the force sensor is an accelerometer which directly measures acceleration and outputs acceleration data which may be converted to force data. In some aspects, a plurality of devices of the invention form an array, with each impulse hammer in the array delivering pulse data from its impact to the computer, and for each individual pulse data the computer determines whether the laminate structure is in a bonded state or a debonded state. Such an array may be equipped further with a means of marking regions, for example, marking debonded regions with visible markings. In other aspects, the array may additionally be equipped with means to crawl on the laminated substrate such that it may conduct sampling of many regions sequentially and/or automatically.

In some aspects, the invention is a method for determining a bonded or a debonded state between layers of a laminate structure, which method has steps of impacting a region of the laminate structure with a pulse hammer for a time period, where the force versus time pulse data has a plurality of data points spanning fractions of the time period, receiving force versus time pulse data from a pulse hammer having a force sensor; normalizing the pulse data to produce a normalized pulse curve; and calculating a pulse RMSD by comparing the normalized pulse curve to a universal profile. If the pulse RMSD exceeds the profile threshold, the laminate structure is determined to be in a debonded state, and if the pulse RMSD does not exceed the profile threshold, the laminate structure is determined to be in a bonded state. In other aspects, the pulse RMSD is calculated according to $$RMSD = \sqrt{\frac{\sum (f^*(t^*) - P(t^*))^2}{N}}$$

wherein f* is a nondimensional force, t* is a nondimensional time, f*(t*) is the normalized pulse curve, P(t*) is the universal profile, and N is a number of time points in the pulse data.

In some aspects, the universal profile for use in the method of the invention is generated by the steps of subjecting a plurality of normalized pulse curves to a mathematical regression to establish a plurality of parameters parametrically describing each of the normalized pulse curves; averaging each of the parameters to produce a working profile; comparing each normalized pulse curve to the working profile to produce an RMSD for each normalized pulse curve; generating a working profile histogram comprising the RMSDs; and iteratively eliminating outlier pulse RMSDs to refine the working profile until a confidence level is reached. After the last outlier is eliminated, the working profile is refined one last time and this last refined working profile is deemed to be the universal profile.

In some aspects, the mathematical regression is a nonlinear regression, while in others it is a linear regression. In other aspects of the invention, a nonlinear regression is used, according to $$f^*(t^*) = p_1 + p_2 \sin(p_3 t^* + p_4) e^{-p_5 t^*}$$

wherein f* is a nondimensional force, t* is a nondimensional time, $p_1$ is a DC offset to long-term equilibrium position, $p_2$ is a mean-to-peak amplitude, $p_3$ is a ringdown frequency, $p_4$ is a phase, and $p_5$ is an energy dissipation term calculated as a product of a viscous damping ratio and a natural frequency. In other aspects, the RMSD is calculated according to $$RMSD = \sqrt{\frac{\sum (f^*(t^*) - p(t^*))^2}{N}}$$

wherein f* is a nondimensional force, t* is a nondimensional time, f*(t*) is the normalized pulse curve, p(t*) is the working profile, and N is a number of time points in the pulse data.

In some aspects, the method also employs a plurality of devices mounted in an array. Each impulse hammer's impulse hammer head is mounted on, for example, an air cylinder, and the air cylinders are controlled by a controller capable of triggering an impact of the head against the laminate structure. The method also includes the step of triggering impacts at more than one location of the laminate structure, and at each location the bonded or debonded state is determined. Debonded locations may be marked with, for example, paint, for easy identification.

These and other aspects of the invention will be readily appreciated by those of skill in the art from the description of the invention herein.

DETAILED DESCRIPTION OF THE INVENTION

Figure 1:
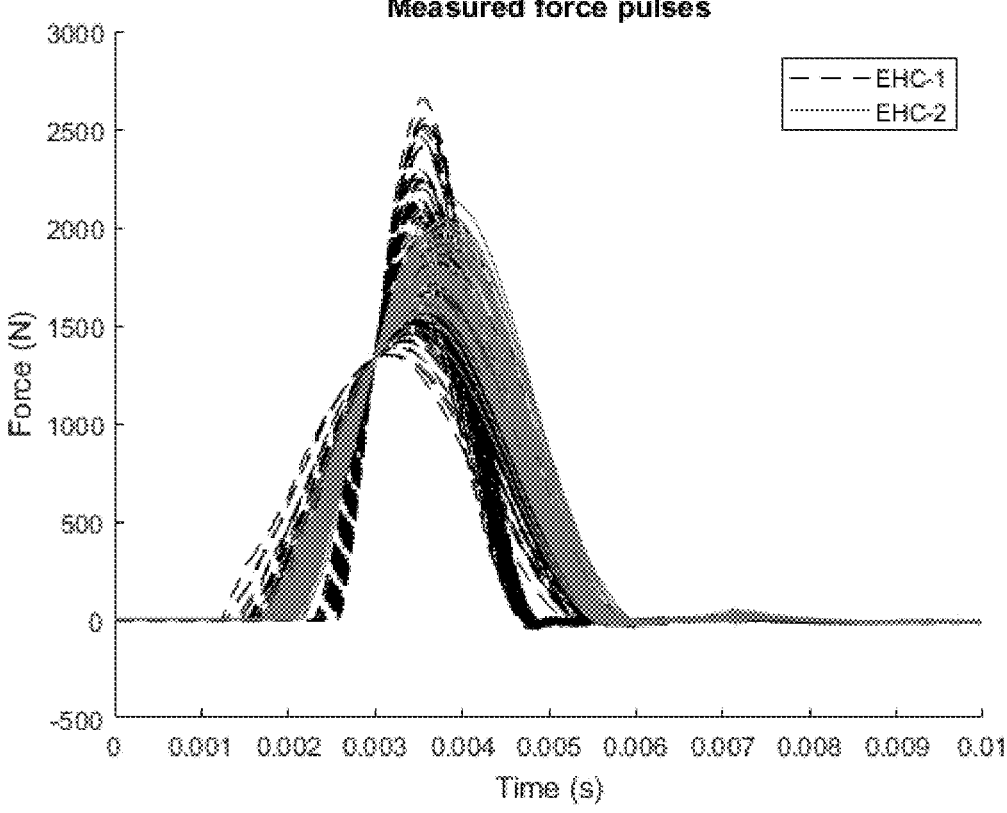
FIG. 1 depicts measured force impulse traces of impacts in an embodiment of the invention.

The HAMSTER system captures and uses the force data from an impulse hammer following its impact with laminated substrate, limiting the variables to be analyzed by focusing on the time dimension. The data is processed such that debonding is detected with high accuracy. The HAMSTER device does not require calibration, is not sensitive to orientation or temperature, and may be used in different environments including air and water. While the invention is described in further detail below with respect to an EHC laminate on a ship hull, those of skill in the art will appreciate that the methods and devices of the invention are equally adaptable to many substrate-laminate combinations.

In its simplest embodiments, the invention provides a nondestructive test method wherein an operator taps a region of, for example, EHC-coated hull, with an impulse hammer using minimal force and an easy swing (for example, less force than a typical hammering of a nail into wood). The impulse hammer is equipped with a force sensor in its head and is designed to be capable of measuring force at impact. One example of such a handheld impulse hammer is the PCB Piezotronics Model TLD086D20, described in its Installation and Operating Manual, which is incorporated herein. The electrical output from the hammer impact is passed to and processed by a computer, generally one or more microprocessors, situated in an enclosure or box wearable by the operator.

The HAMSTER system programmed into the computer normalizes the pulse captured pulse data, compares the normalized pulse data to the HAMSTER profile, and calculates a root mean square difference for the pulse, which indicates the extent to which the normalized pulse deviates from the profile. The HAMSTER system determines whether the extent of such deviation exceeds the profile threshold, and thereby provides a determination of the bonding condition. The user is then notified if the EHC is in a debonded state. Optionally the system can provide a discrete notification indicating a bonded state or a debonded state. The complete process is rapid, taking on the order of about one half second, and results in informing the user of the bonding condition of the EHC with high accuracy. Only one sensor is required for each impulse hammer, rendering the process simple, fast, and efficient. In addition, a typical handheld HAMSTER user-ready impulse hammer weighs between 2 and 3 pounds, and requires very little force to wield, thereby minimizing user fatigue. Shipyard personnel may survey an entire hull with little effort, at a fast rate, and with accurate findings.

The processing of the impulse hammer's data is achieved via computer either onboard (i.e., contained within the impulse hammer itself) or outboard (i.e., contained in an external enclosure connected to the HAMSTER hammer). The notification to the user can be accomplished in a variety of ways, including but not limited to simple LED(s) (onboard or outboard) illuminating to indicate bonded or debonded states, generating audible signals, providing tactile feedback in the impulse hammer itself, and/or relaying the information to another device. The notification may also be transmitted via wire or wireless communication to a remote observer or data logging system.

The invention has numerous advantages over previous methods. The HAMSTER provides high accuracy, rapid and simple collection of data, and high reliability. The HAMSTER allows an EHC coated hull to be surveyed in essentially its entirety by users with handheld devices. Older methods provided for surveys approaching far less of the hull (on the order of 10%) due to the limitations of the tool and time constraints. It is also expected that the HAMSTER costs far less than current tools.

In other embodiments, the impulse hammer may not be handheld but rather mounted on a frame or the like, automated, and/or robotically controlled. Such mounted impulse hammers are adapted to trigger at a specified force without the need for an operator manually swinging the hammer. In such embodiments, the force of impacts may be more repeatable, not being subject to the varied forces imparted by an operator using a handheld impulse hammer. However, the HAMSTER system performs well with handheld operation so long as the impact force is greater than a low trigger force and less than an overload force. Compliance of a swing is monitored by the HAMSTER system, which may indicate to the user a swing outside the range.

In still other embodiments, a plurality of such impulse hammers may be mounted on a frame forming an array such that multiple impacts may be collected simultaneously and larger regions may be inspected more quickly than with single handheld impulse hammers. The plurality of impulse hammers would be triggered to impact, which triggering may be performed automatically at programmed regular intervals, or may be initiated by an operator controlling the array. Further, the frame carrying the array may be provided means of moving about the hull, such as a crawler, optionally automated or remotely operated as well. The array may be equipped with a means of marking debonded regions for subsequent repair, such means being readily appreciated by those of skill in the art. Alternatively, the resulting indications of bonding states may be compiled into a virtual map of the delaminated regions requiring repair. Such a map may be stored onboard the array, or may be communicated to another device.

The HAMSTER is thus adaptable to a wide variety of uses. It may be utilized for testing substrate-laminate combinations such as the bodies of aircraft bearing particular laminate coatings, construction-related bonding in flooring and walls, and the like.

The HAMSTER System

The HAMSTER system is described below with reference to the substrate being a metal hull and the laminate being EHC, but those of skill in the art will appreciate that the HAMSTER system is equally applicable to a wide range of substrate-laminate combinations.

Where EHC is fully bonded to a hull, there is no gap between the outer surface of the hull and the hull-facing surface of the EHC, and the boundary between the hull and EHC permits no freedom of movement therebetween; they are firmly affixed. In response to an impact on the exterior surface of the EHC with an impulse hammer, the EHC has no freedom to move in the direction of the impact, nor sideways in relation to the surface of the hull, and will therefore initially compress under the force of the impact. It will continue to compress until it reaches peak compression. After peak compression, the EHC begins to decompress (i.e., the restitution phase), until it is fully decompressed and the hammer is no longer in contact. Force measurements can be collected throughout the operation, from the time before initial impact, through impact, compression, restitution, and finally with the release of the hammer from contact with the EHC, returning to rest.

The HAMSTER system detects bonding and debonding relying on the fact that measurements with an impulse hammer focused in the time domain can detect the presence or absence of defects in the bonding (e.g., physical gaps or other defective boundary conditions between the substrate and laminate) through analysis of the force versus time data collected during the impact operation.

The EHC and the head of the instrumented impulse hammer form a mass/spring/damper mechanical system. As the hammer impacts the EHC surface it has an initial velocity, but at that moment there is no compression (displacement) of the EHC. The force gauge in the hammer head measures the reactive force of the EHC on the hammer head as a function of time, and because there is no compression, there is also zero force measured at the instant of impact. Likewise, in embodiments having a force sensor using an accelerometer, acceleration is also zero at the instant of impact.

During the compression phase of the impact the kinetic energy in the hammer head is transferred into elastic energy in the EHC, the EHC compresses, the velocity of the hammer begins to decrease, and the measured force concomitantly rises (just as an accelerometer would measure acceleration rising from the initial zero). At the peak of compression the hammer's velocity is zero and the measured force (or acceleration) reaches its maximum. During the restitution phase the EHC relaxes (decompresses) and transfers energy back into kinetic energy in the hammer. At the instant the hammer head leaves the EHC the EHC is uncompressed and the measured force has returned to zero.

During the complete compression/restitution operation some energy is dissipated due to hysteresis in the EHC and other energy losses.

Where EHC has become debonded, however, even to a very small extent, a defect (e.g., a gap or other debonding artifact) exists between the outer surface of the hull and the hull-facing surface of the EHC. That defect causes a change in the measured pulse curve upon impact with an impulse hammer. During impact, rather than only a compression and decompression, the EHC may move in response to the impact. Where there is a debond, the EHC may move toward the surface of the hull, closing an actual gap, or slide along the hull when the boundary is defective, or may otherwise respond to an impact differently from well bonded EHC. In the case of a physical gap, for example, the EHC compresses only when the gap has closed. The presence of the gap, and the associated freedom of the EHC to move, changes the force measurements from those which would be expected if the EHC was well bonded to the hull surface. Instead of matching the universal profile pulse curve for well-bonded EHC, the presence of a bonding defect causes the pulse curve to deviate because the rises and falls in force during impact are changed by the presence of the defect. Particularly when the defect is a physical gap, HAMSTER may need only to examine the force measurements from the early phases of the impact to "see" the debonded EHC's pulse curve deviate from the pulse curve of well-bonded EHC because the presence of the gap mostly affects the pulse curve prior to the compression phase. After any movement to close a gap or otherwise move, compression, and decompression/restitution, the EHC may move away from the hull surface, providing another point of deviation from the pulse curve of bonded EHC.

The HAMSTER system is designed to use the characteristics of the pulse curve resulting from an impact to determine whether there is a bonded state or debonded state. Prior to testing any particular region, a HAMSTER profile is generated, which mathematically describes the profile pulse curve parametrically. A number of parameters may be derived from such parametric description, depending on the particular profiling being used. In some embodiments, five distinct parameters are used to describe a profile pulse curve. In other embodiments more parameters may be used, such as ten, or fifteen, or more. A profile threshold is chosen based on a desired level of confidence, the threshold being the level of deviation from the profile pulse curve (as measured by RMSD) a sample pulse curve must exceed for the system to conclude that the impact site is debonded. The profile and threshold are programmed into the HAMSTER computer hardware. Using the impulse hammer, the user strikes a region of EHC coated hull, generating a sample pulse. The HAMSTER system then calculates whether the new pulse deviates from the profile to determine whether the profile threshold has been exceeded and thereby determines whether there is a bond or debond.

Pulse Analysis

Analysis of a pulse generated by an impact by the impulse hammer can be modelled with a variety of mathematical functions. One exemplary model is a linear single degree of freedom system using equation (1).

$$m\frac{d^2x}{dt^2} + c\frac{dx}{dt} + kx = 0 \tag{1}$$

In equation (1) m is the effective mass of the system; c is a viscous damping coefficient, an energy dissipation term; and k is the effective stiffness of the EHC. As described below, the numeric values for these parameters do not need to be known for the HAMSTER system to produce its result, that is, whether the EHC is bonded or debonded. Equation (1) represents a system with no external forcing function. This may appear counterintuitive because the hammer is in fact impacting the EHC. However, the measured force is an internal force, internal to the system of the EHC and hammer combined. The solution is therefore a classic vibration "ring down." The solution to equation (1) now has the form shown in equation (2).

$$x(t) = a_1 + a_2 \sin(a_3 t + a_4) e^{-a_5 t} \qquad (2)$$

The values of $a_1$ through as are the five parameters required for this particular profile function. The offset term, parameter $a_1$ in equation (2), is included to permit different origins for the displacement (e.g., the surface of the EHC rather than the equilibrium vibration position). In accordance with classic vibration theory the parameters $a_1$ to $a_5$ relate to, respectively: DC offset to long-term equilibrium position; mean-to-peak amplitude; ringdown frequency; phase; and energy dissipation term calculated as the product of viscous damping ratio and natural frequency.

The force measured by the force gauge is a measure of the force applied to the stiffness of the EHC. As described above, as used herein, the measured force means the directly measured force in embodiments using a force sensor outputting measured force, or the indirectly measured force calculated by f=ma from a directly measured acceleration in embodiments using an accelerometer as the force sensor. Equation (3) is derived from equation (1) to reveal the internal measured force versus time f(t).

$$f(t) = -m \frac{d^2 x}{dt^2} = c \frac{dx}{dt} + kx \qquad (3)$$

In the implied coordinate system with x being positive into the EHC, in equation (3) the minus sign recognizes that the velocity of the impulse hammer during impact diminishes. That is, the impulse hammer experiences an acceleration directly opposite the direction of impact, outward away from the EHC surface.

One makes the assumption that damping is light based on experience with EHC and many other substrates. Equation (4) can then be derived from equation (3) and the measured force is thus seen to be an indirect measurement of displacement.

$$x(t) = \frac{f(t)}{k} \qquad (4)$$

Every combination of initial hammer speed, EHC material, EHC thickness, and substrate stiffness would be expected to yield a different pulse curve. For example, softer EHC material will stretch the measured pulse curve over a longer time because the compression and restitution phases would take longer, as would a thicker section when compared with a thinner section. This is demonstrated in FIG. 1 which overlays actual measured pulses from a submarine in dry dock measuring two different EHC materials, denoted EHC-1 and EHC-2. FIG. 1 shows that peak amplitudes vary with the (unmeasured) speed of the hammer, and also that the pulse width (duration) varies. Regions with softer EHC (either a softer material and/or thicker) show a wider (slower) pulse, whereas stiffer regions have a shorter pulse width.

The data for each pulse includes the force measured for each time point. Depending on the particular HAMSTER device being used and the desired precision, the data captured may be sampled at a wide range of time intervals. For example, in some embodiments, the sampling rate is 50,000 data points per second. In other embodiments, the sampling rate is more than 150,000 data points per second. The duration of a typical impact by the impulse hammer from initial to final contact is on the order of about 5 milliseconds, but may range from about 3 milliseconds to about 10 milliseconds. Depending on the sample rate, a typical pulse will thereby generate from about 150-500 time points with associated force measurements at a sampling rate of 50,000 per second, or 300-1,500 time points with associated force measurements at a sampling rate of 150,000 per second. Higher sampling rates produce yet higher numbers of time points. However, even at lesser samples, for example, 150 time points, the HAMSTER is capable of distinguishing bonded from debonded states through calculation of a deviation compared to the profile.

The intersection of all measurements at approximately 0.003 seconds and 1300 Newtons is caused by the HAMSTER data acquisition system. For the measurements depicted in FIG. 1, the analyzer was set to trigger when the force level reached 1300 Newtons, with a pretrigger of three milliseconds. Thus all measured data must necessarily go through that point, which is a setting established in the system.

Figure 2:
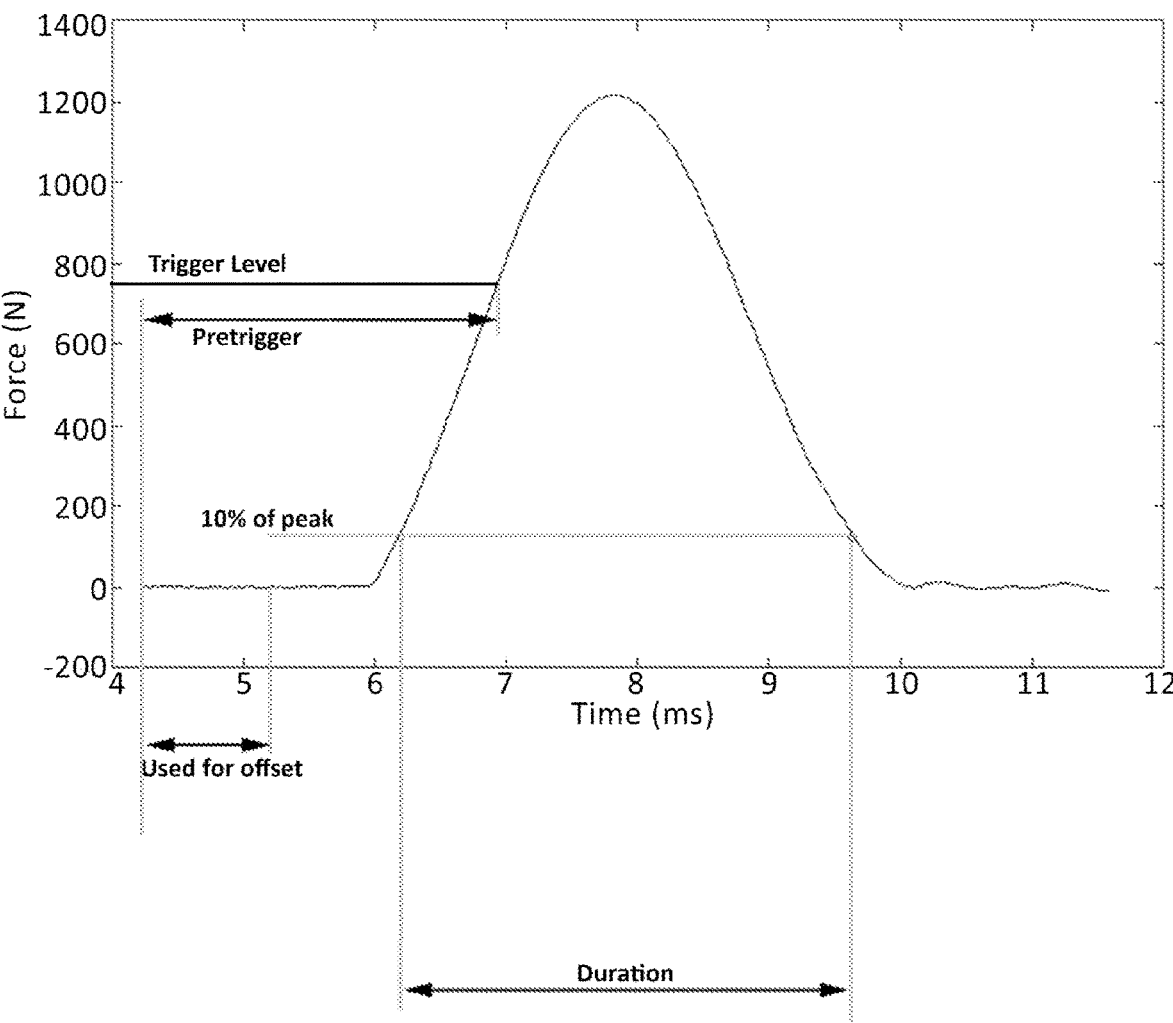
FIG. 2 depicts a force impulse trace of an impact in an embodiment of the invention, identifying portions of the impulse.

Normalization may be used to reduce the apparent variability caused by different EHC and hull materials and different initial hammer impact forces. The normalization is performed for both time and total impulse force. Such a normalization procedure generally is achieved as follows:

Only the data for when the force is greater than 10% of the peak measured force are retained. This portion of the pulse curve is called the duration of the pulse and is depicted in FIG. 2 along with additional characteristics of a force pulse curve trace. The use of 10% of peak to mark the start and end of the pulse is consistent with standard shock test procedures, but the actual percentage used is not critical for HAMSTER. Other percentage ranges may be used in different embodiments and for different materials. Additionally, different conditions may dictate the use of different ranges. For example, using HAMSTER to impact EHC on a submarine hull underwater, a more effective range may be 20%-20%, 10%-60%, or other, as determined by routine experimentation.

The time axis for the duration of the pulse is then time warped, such that the pulse starts at zero and finishes at one. All normalized pulse curve traces therefore have a 0-1 time axis, which is accordingly called "nondimensional time."

The time-warped pulse curve is then impulse-scaled in amplitude such that the area under the pulse is one. This is conceptually equivalent to dividing the force by the measured impulse, since impulse is the integral of force versus time. The resulting force magnitudes are now accordingly called "nondimensional force."

Figure 3:
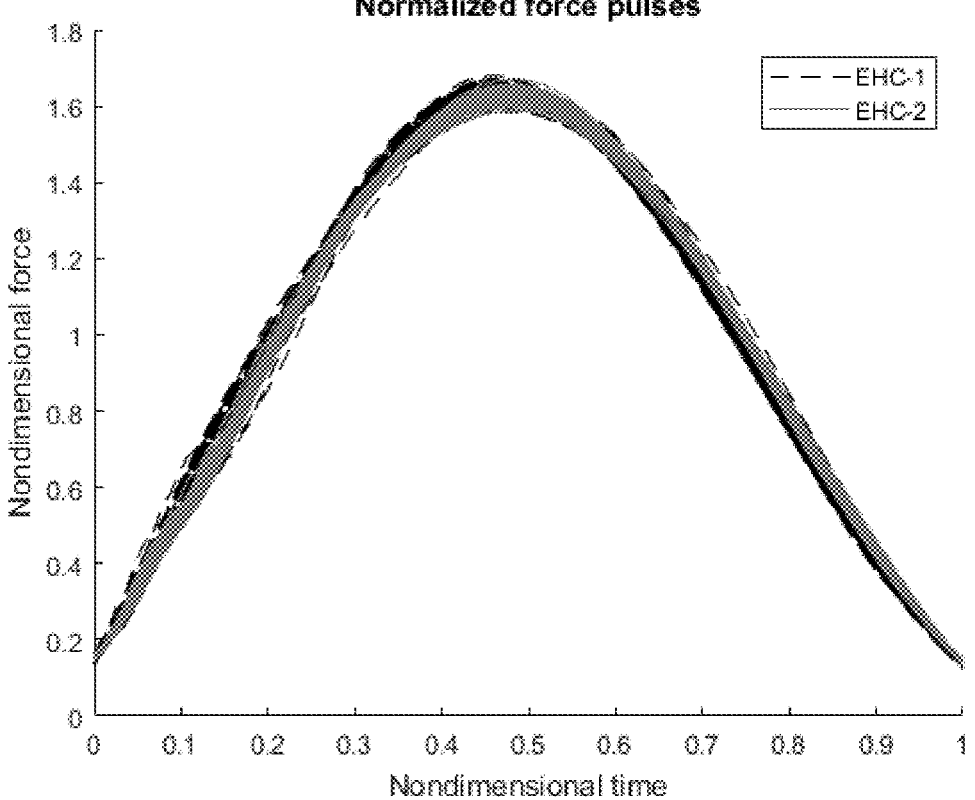
FIG. 3 depicts normalized force impulse traces of impacts for two materials in an embodiment of the invention.

The normalized pulse data for the data in FIG. 1 are shown in FIG. 3. The variability from impact to impact, as well as the variability between the two materials with different hardness/stiffness characteristics, are substantially reduced. The normalized pulse curve traces all show a similar form, regardless of EHC material. One strength of HAMSTER is that one may derive a universal profile that all normalized (i.e., time-warped and force scaled) impulse curves will follow, provided that the tested area is well bonded, while measurements from a debonded region will yield normalized impulse curves which deviate from the profile.

The HAMSTER Profile

Even for well bonded regions of EHC there will be different "ring down" shapes for different levels of hammer impact (the force with which the user swings the hammer), different EHC thickness and materials, and different locations on the hull. Applying the time warping and impulse normalization techniques, the HAMSTER system uses the fact that all normalized force versus time pulses measured from bonded EHC have nearly identical shapes. This common shape, with the parameters mathematically defining the shape, becomes the HAMSTER profile. This profile is the non-varying pulse curve against which measured force pulses can be compared.

One significant advantage of the HAMSTER normalization process is that the force transducer built into the impulse hammer does not have to be calibrated because the system is not dependent on the force transducer's sensitivity. Should an impulse hammer fail during operation (e.g., if it were dropped or otherwise broken), it can be replaced by another without having to reprogram the system with the new hammer's sensitivity. Likewise, because the system is insensitive to the force gauge sensitivity, there is no need to recalibrate the system as the operator moves from location to location.

The HAMSTER profile is the standard normalized pulse curve against which measured (and normalized) force pulses are compared. The profile can be derived by averaging all the normalized traces from many measurements of a substrate, for example EHC. The average normalized pulse is then the working profile for the EHC. The profile can be expressed in parametric form by subjecting the averaged pulse data to a mathematical regression, such as the nonlinear regression of equation (5).

$$f^*(t^*) = p_1 + p_2 \sin(p_3 t^* + p_4) e^{-p_5 t^*} \qquad (5)$$

In equation (5), f* is the nondimensional force and t* is the nondimensional time. The parameters $p_1$ through $p_5$ relate to, respectively: DC offset to long-term equilibrium position; mean-to-peak amplitude; ringdown frequency; phase; and energy dissipation term calculated as the product of viscous damping ratio and natural frequency.

Using equation (5) for many pulses and averaging them, these parameters $p_1$ through $p_5$ can be calculated and then the parameters represent a mathematical definition of the profile. The force for all time points in an impulse curve are thus derivable from this universal profile. New measured impacts produce force-versus-time pulses which are then normalized and compared with this profile. Significant deviation from the profile indicates a potential debond or other anomaly in the EHC.

In order to identify the universal profile, it is helpful to analyze many force pulses measured from a variety of EHC materials, hull locations, and different hulls. However, ideally only measurements from well-bonded regions of EHC should be used as part of a profile that will be useful to discriminate between bonded and debonded regions of EHC. If one knows regions where the EHC is well-bonded, one could simply collect measurements from a sufficiently large number of impacts with the HAMSTER impulse hammer and average the data to generate an effective profile.

In the laboratory one may prepare a known region of well-bonded EHC, conduct impacts with the HAMSTER system, and build a profile. The inventors built such a profile and proved HAMSTER to be effective in identifying bonded and debonded EHC. But in the field, for example, at a shipyard preparing to inspect a ship, known regions of well-bonded EHC may be difficult to identify. Those of skill in the art will appreciate that an alternative means of formulating the profile may be achieved. Based on the fact that impacts on well-bonded regions will generate normalized pulse curves conforming to a certain shape, one may build a working profile by identifying that shape and iteratively removing outliers whose pulse curves do not conform (representing debonded regions), and then regenerating a new working profile. With each iteration the profile becomes more precise and more accurately represents the pulse curves from bonded regions, until ultimately the working profile is sufficiently precise to be termed the global or universal profile.

As described herein, the inventors built a profile using this method, measuring a large number of force pulses from a variety of hull locations. Each pulse was separately normalized and subjected to a nonlinear regression of equation (5). The working profile parameters were then determined as the average of each of the separate parameters $p_1$ through $p_5$.

At this stage of the calculation, data from both bonded and debonded areas was included in the working profile. Therefore, each normalized pulse was then individually compared with the profile to numerically determine its deviation from the working profile. This was determined using a Root Mean Square Difference (RMSD) calculation between the normalized pulse and the current working profile, as shown in equation (6), where P(t*) is the average of all the f(t*) pulses evaluated at nondimensional time t* and N is the number of points in the normalized force pulse f*.

$$RMSD = \sqrt{\frac{\sum (f^*(t^*) - P(t^*))^2}{N}} \qquad (6)$$

Figure 4:
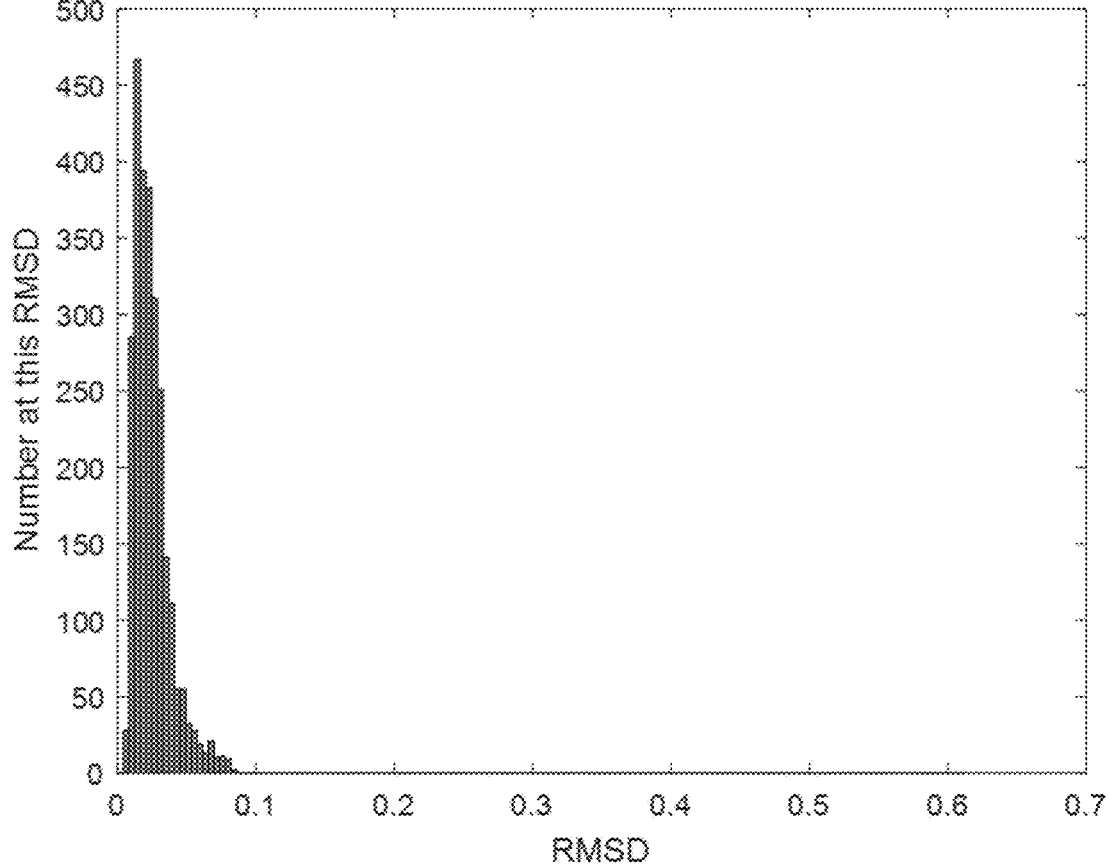
FIG. 4 depicts an RMSD histogram in an embodiment of the invention.
Figure 5:
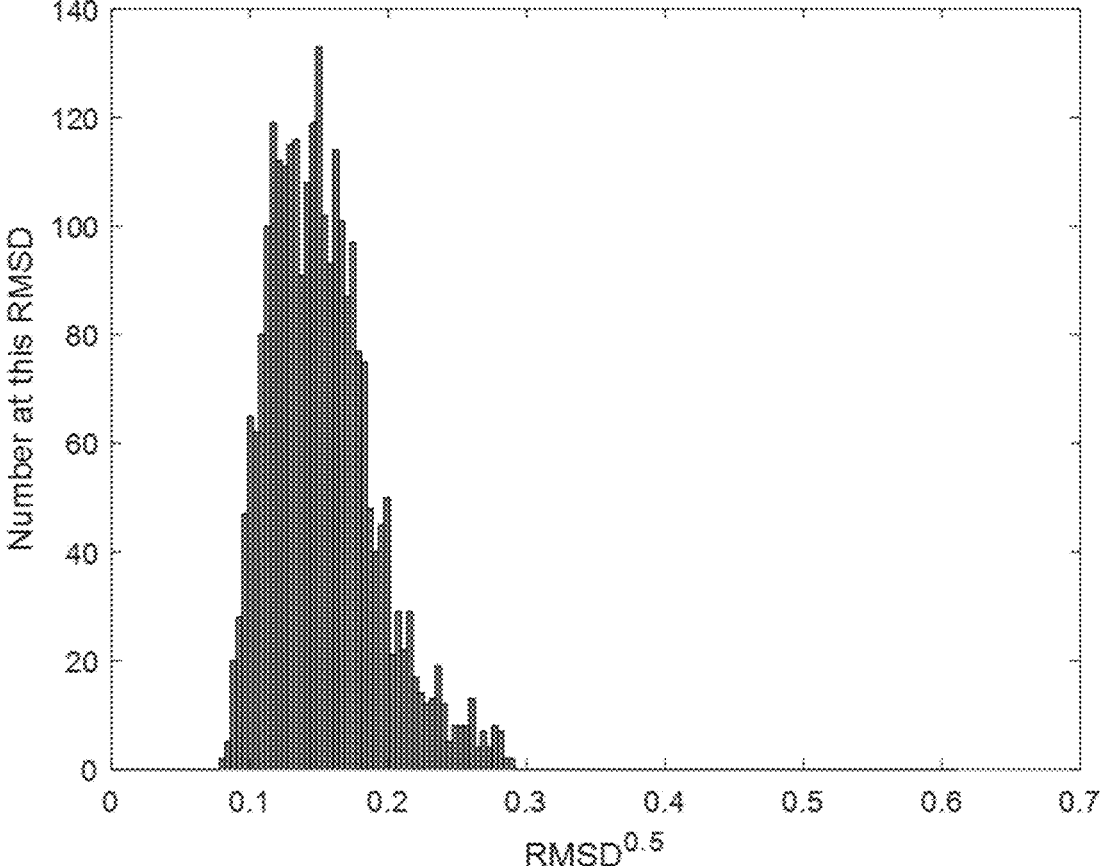
FIG. 5 depicts a square root RMSD histogram in an embodiment of the invention.

As an example, the RMSD calculated for 2714 force pulses measured from a Naval vessel bearing EHC are shown in the histogram in FIG. 4. While many of the RMSD values appear to cluster near RMSD of 0.05, there are also many outliers. The histogram also shows significant right skewness. Since the RMSD values are calculated in equation (6) from a squared quantity, the histogram will never show a negative RMSD. This has the effect of making the histogram appear more like a Chi² distribution function than a normal distribution function. Recalling that when data for a normally distributed function are squared they form a Chi² distribution, one may transform the data shown in FIG. 4 by taking the square root of the RMSD calculated by equation (6) to form the histogram in FIG. 5. This histogram appears more normally distributed (although there are still no negative values) and is more amenable to outlier elimination.

The outliers are indicative of a measurement at a debonded region. Therefore, the outliers need to be removed prior to recalculating an improved working profile. In determining a universal profile, an outlier elimination routine is used. One measurement at a time is eliminated, and a new profile is determined as before (each profile parameter was calculated as the average of the parameters for each of the included normalized pulses). The RMSD between the remaining measurements and the new profile are then determined, and the process is repeated until no more outliers are identified. This ensures that only measurements from bonded areas are used in forming the universal profile.

Figure 6:
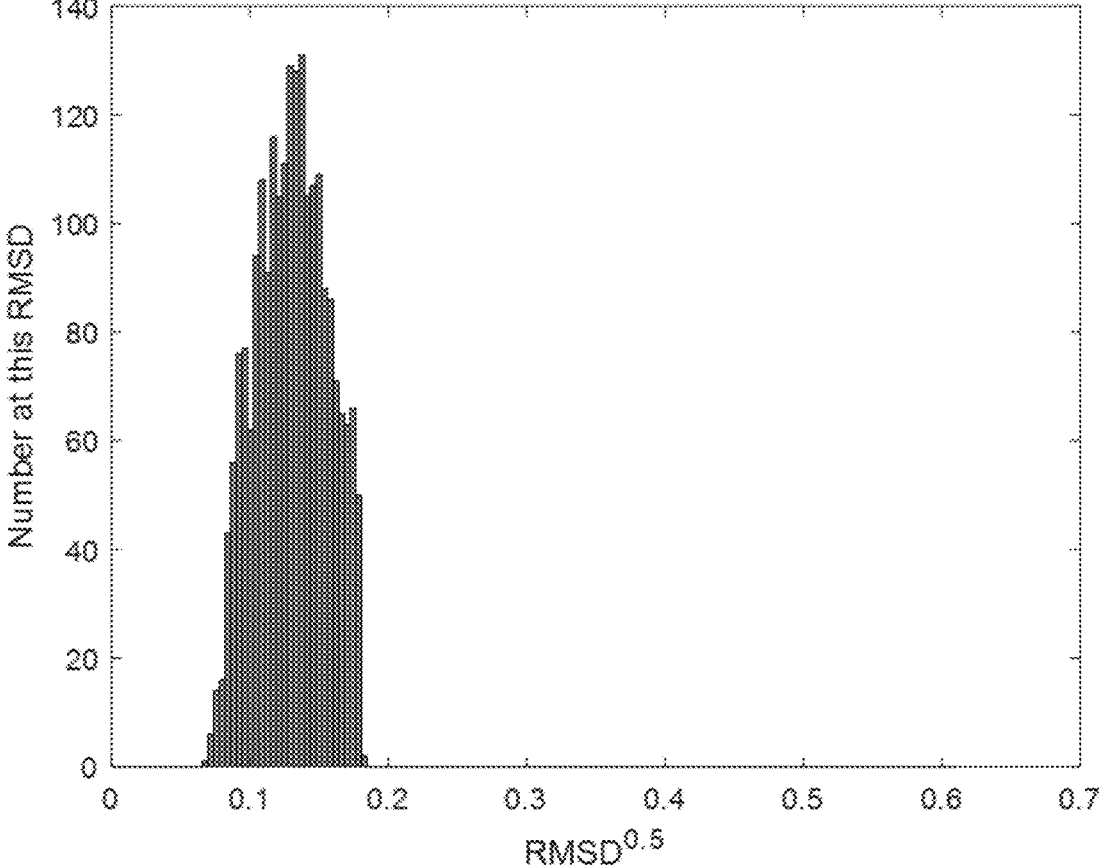
FIG. 6 depicts a square root RMSD histogram after outlier removal in an embodiment of the invention.

For this example, the outlier elimination routine chosen was the iterative Thompson-tau method which eliminates one outlier per iteration, although other suitable methods may be used successfully. After each outlier is eliminated, the process is repeated, with a revised working profile being determined from the average of the remaining f(t*) pulses. The outlier elimination iteration is continued until there are no more identified outliers. FIG. 6 shows the same data as FIG. 5 after outlier elimination using a 99% level of confidence. After outliers are eliminated in accordance with the desired level of confidence, the profile is complete. A nonlinear regression of the profile P(t*) yields the five universal profile parameters $p_1$ through $p_5$. For comparing the force pulse curve data from a new impact, the profile force for any given time point may be derived from the parametric equation.

The HAMSTER Threshold

The HAMSTER threshold is a value held in the system representing the RMSD of pulses specifying the boundary between bonded and debonded measurements within the desired level of confidence. When measured pulses are processed, their RMSD values are calculated in comparison with the profile. If the measured value exceeds the HAMSTER threshold a debond is declared. If the measured value is less than the threshold, the region is declared to be bonded. For example, the RMSD threshold value for a 99% confidence level for data acquired from another Naval vessel was 0.039. Thus, if the RMSD for a pulse exceeds 0.039 it is a debond location; otherwise there is no presumed debond. Profile parameters and threshold values may be refined as more data is collected.

The threshold may be further refined statistically from a history of different EHC materials, locations, vessels, and HAMSTER operators. As more data and shipyard feedback becomes available, it is anticipated that the threshold values will be fine-tuned to improve the HAMSTER performance, but given the confidence levels applied during the development of the profile, no significant changes are anticipated.

The threshold RMSD value depends upon the level of confidence desired for detection of debonded regions. Depending on the nature of the inquiry, and the criticality of detection, one may choose higher or lower confidence levels. Higher confidence levels identify debond states with higher confidence, and concomitantly are less sensitive to and less inclusive of borderline bond-debond states. Conversely, lower confidence levels identify debond states more inclusively, and will capture more borderline bond-debond states. One thus chooses the level of confidence for threshold setting depending on the particular application of HAMSTER. For the most critical detection of debonds where one needs to insure capturing all debonds, one would use a lower confidence level in order to identify all debonds, with the known likelihood of including borderline cases which may in fact be bonded. For less critical detection of debonds, a higher level of confidence still captures the debonded regions, but includes fewer borderline cases which may in fact be bonded. Nonetheless, in practice the HAMSTER system proved accurate even at varied confidence levels. In testing the HAMSTER system as more fully described below in Example 1, it was found that in one limited testing sample, varying the confidence level from 80% to 99% resulted in zero changes to the detected bonding states. In a second broader testing of more samples, varying the confidence level from 80% to 99% resulted in less than 0.1% altered states detected.

HAMSTER Used for Detection of Debonded Regions

Once a universal profile is established as described above, and the appropriate threshold is chosen for the particular application, HAMSTER may be employed to detect debonded regions of laminate. The user strikes a region of laminated substrate with a HAMSTER impulse hammer, which sends force versus time data to the computer. If the user swung with too little force (less than the trigger setting) for the HAMSTER system to gather the necessary data, the user is notified and must swing again with greater force. Similarly, if the user struck with too great a force (over the overload setting), the user is notified and must swing again with less force. Alternatively, in some embodiments, the HAMSTER system notifies the user that a swing is "good" when sufficient force is applied. In such embodiments, swings with force outside the acceptable range fail to generate the "good" notification, thereby alerting the user to swing again but with greater or lesser force. In other embodiments, notifications are provided for two of the three possible force conditions: too little, in acceptable range, and too much.

The computer processes the pulse data by normalizing (time-warping and force scaling), producing normalized pulse curve data of nondimensional force versus nondimensional time. The computer then compares the normalized force measurements with those derived from the universal profile, using equation (7) (analogous to previously described equation (6)) to calculate the RMSD for the pulse:

$$RMSD = \sqrt{\frac{\sum (f^*(t^*) - P(t^*))^2}{N}} \qquad (7)$$

where P(t*) is the universal profile evaluated at nondimensional time t* and N is the number of points in the normalized force pulse f* being compared to the universal profile.

The calculated RMSD is a measure of the deviation of the newly recorded pulse curve data from that of the universal profile. If the RMSD is greater than the threshold, the laminate is determined to be debonded from the substrate and the user is notified. If the RMSD is below the threshold, the laminate is determined to be bonded, and the user is optionally notified.

The following Examples serve to illustrate the present invention and are not intended to limit its scope in any way.

EXAMPLES

Example 1: Construction of a HAMSTER Device

The HAMSTER system makes use of the following activities.

Impulsive force excitation. A PCB model TLD086D20 sledge impulse hammer was used in this Example. The pulse hammer includes a handle, piezoelectric force gauge, and BNC connector for the gauge. The gauge has a nominal sensitivity of 0.23 mV/N, with a peak force of 22,240 N. The hammer is powered by a PCB model 480C02 signal conditioner. The hammer weighs 2.4 lb.

Computers and microprocessors. During initial experimentation the data were acquired using an Oros signal analyzer controlled by a laptop computer. Such a system may be used in appropriate environments, but may prove to be ill-suited for shipyard use due to high cost, complexity, required mains electrical power supply, fragility, and the relatively high level of required training. The microprocessor chosen for this Example HAMSTER for field use was an Arduino Due. The Arduino Due is a microcontroller board based on the Microchip SAM3X8E Arm Cortex-M3 CPU. It is the first Arduino board based on a 32-bit ARM core microcontroller. The Due has 54 digital input/output pins (of which 12 can be used as PWM outputs), 12 analog inputs, four UARTs (hardware serial ports), an 84 MHz clock, a USB OTG capable connection, two DAC (digital to analog), two TWI, a power jack, an SPI header, a JTAG header, a reset button, and an erase button. Other potential microprocessor systems include, for example, Raspberry Pi systems.

Data acquisition. Using the Arduino Due microprocessor, the analog-in pin can accept up to 3.3V, which is sufficient for this system. An overload fuse may be included for protection. The Arduino Due microprocessor samples the force pulse at approximately $140 \times 10^3$ samples per second, although the data capture rate is slightly lower because some CPU cycles are needed for control. Additionally, the impulse hammer's force gauge is an IEPE transducer. Signal conditioning for IEPE transducers inherently includes a DC offset of approximately 10 Volts. Laboratory based signal conditioning and data acquisition settings do an excellent job of removing this DC offset. The analyzer was set to trigger when the force level reached 1300 Newtons, with a pretrigger of 3 milliseconds Data analysis. During initial development data files were stored from the Oros system and then imported into MATLAB. All analysis was then conducted using MATLAB. MATLAB gives the flexibility of being able to rapidly change algorithms, plot graphs and perform other complex analysis. However, for a functioning field use HAMSTER, this level of complexity is unnecessary. Instead, for this example, two arrays of LEDs (one blue, one red) were built in to the back of the impulse hammer's head for notification and communication with the operator. Simplified code was rewritten in Arduino's variant of C++ and then uploaded to the microprocessor.

Archiving data. While HAMSTER does not require archiving of data, this system was equipped with a micro SD writer. Every measured force pulse was automatically saved to a micro SD card. Should it be necessary or desirable to post-process any of the data (for example, to refine the profile), the SD card can be made available for such. In addition to the actual force versus time pulse history, each data file includes the serial number of the HAMSTER system in use, the date and time of acquisition, and the profile parameters in use. Each 32 GB SD card can hold more than 900,000 data sets which would occur if the operator hit the EHC once per second, every second, for 11 days continuously.

Power. For this Example of HAMSTER, the microprocessor and hammer signal conditioner are powered by a rechargeable Li-ion battery pack which can operate continuously for several days between charges. Other embodiments may utilize different power packs, such as non-rechargeable batteries.

Connectivity. For this field use HAMSTER, the impulse hammer is connected via a sufficiently long cable (coiled if desired) to the HAMSTER enclosure box. The connectors chosen for this HAMSTER are 5-pin XLS type. Two wires are for the hammer, and the remaining three wires are for the LEDs built into the hammer head. Inside the HAMSTER box the signal conditioning output is connected to an Adafruit data logger shield as an analog input. An analog high pass filter with a 3 dB frequency of about 1.5 Hz was built into the analog circuitry embedded on the Adafruit data shield to prevent false triggers.

In other example HAMSTER devices, the impulse hammer may be adapted to communicate wirelessly with the HAMSTER computer such that the enclosure box may be situated remotely rather than worn by the user. It is also contemplated that in some embodiments of HAMSTER, the impulse hammer itself could be adapted to house all necessary electronics and power, thereby making an entirely self-contained HAMSTER device.

Packaging. The main HAMSTER enclosure box is a Pelican 1120 case, which contains all the electronics and the battery pack. The case was modified by drilling holes to accept the XLS bulkhead connector for the coiled cable. The case was equipped with belt loops so that it can optionally be carried around a person's waist. For storage and shipping the entire system (HAMSTER enclosure box, impulse hammer, and accessories) fits into a Pelican V550 case.

The two LED arrays built in to the impulse hammer's head are referred to as a Ready LED and an Alert LED. When HAMSTER is first powered on, the software reads an initialization file from the SD card which includes details of the HAMSTER profile and threshold. If there is a fault reading the file the two LEDs will alternately flash. While the impulse hammer will still allow the operator to continue to use HAMSTER the system will revert to a default set of parameters. In some embodiments, the LEDs may be designed and wired such that alternative and/or additional indications are provided.

The notification schema selected for this Example HAMSTER is as follows: After initial startup, the Ready LED lights, indicating the system is ready for data acquisition. When the impulse hammer is struck against a surface, the Ready LED briefly flashes quickly, then briefly turns off, indicating an impact was detected and the data is being processed. After an impact and data processing (the software comparing the pulse data acquired with the profile and threshold), the Alert LED informs the operator whether the region is bonded or debonded. If it lights, the area is debonded. If it remains off, the area is well bonded. This schema is tabulated in Table 1:

TABLE 1

| Event | LED sequence |
|---|---|
| HAMSTER active and waiting for a hit | solid ON, either BLUE (last hit on good EHC) or RED (last hit over debond) |
| HAMSTER detects a force pulse greater than the trigger level (1330N). Start capture of a data block. | both LED arrays switch OFF |
| Time block capture complete HAMSTER calculations Alert operator hit was hard enough (but not overloaded) End of operator's "alert time". Repeat from top of list | If "good", rapidly flash BLUE LEDs If "debond", rapidly flash RED LEDs |

The operator need not swing the impulse hammer with a great amount of force. This HAMSTER was configured to alert the operator if the hammer was swung too hard (initially set as greater than 2700 Newtons) by flashing both LEDs alternately for a brief time to indicate an overload condition. The operator is thereby informed that the hammer was swung with too much force, and should repeat with a less forceful swing and impact. The system returns to the ready state for the next impact. The operator then marks regions identified as debonded for later repair and/or removal. In other embodiments, the schema of the LED arrays may be designed and wired such that alternative and/or additional indications are provided.

Depending on the hardware being used (impulse hammer, cables, etc.), signal noise can be a problem. In some embodiments HAMSTER uses a low pass filter to minimize the noise. For example, in embodiments using the well shielded Oros, no low pass filter is used. In other embodiments using an Arduino/Due, HAMSTER uses a 31-point, triangular center weighted, running average low pass filter. Other low pass filters and other means of overcoming such noise will be understood by those of skill in the art and are encompassed within the invention.

When the first HAMSTER prototype was programmed the analysis was so fast that it was necessary to include a delay of about 500 milliseconds between impacts to give the operator time to see HAMSTER's LED alerts. Otherwise the alert (debond or bond) was so fast that it was almost impossible to identify that the hit had been recorded and analyzed. The delay was reduced to 300 milliseconds for this Example's HAMSTER system, which appeared to optimally balance the needs of the operator. The delay may be adjusted as needed.

Example 2: Field Use of the HAMSTER System

The HAMSTER system described in Example 1 was tested on sections of a Naval vessel bearing EHC, in dry dock. The results were compared with those from using the existing Thumper system. The results of HAMSTER and Thumper were verified by removing strips of EHC and visually inspecting whether there was a bond or debond condition. HAMSTER was 100% correct identifying both bonded and debonded regions, while Thumper was 50% correct, incorrectly identifying some bonded areas as debonded and some debonded areas as bonded.

The HAMSTER system described in Example 1 was tested at a shipyard. Untrained personnel were asked to use HAMSTER and give their feedback. Very quickly they were able to become proficient in using the system.

The HAMSTER system described in Example 1 was tested on aft, near keel, non-pressure hull fairing strip and pre-cast tile EHC. A region of the fairing strip and precast tile was marked for removal based on prior testing with another device. HAMSTER's results indicated there was no debond. After the EHC was removed from a portion of the fairing strip and tile, the surrounding area was visually inspected and found to actually be bonded. HAMSTER had correctly identified the region as bonded.

The HAMSTER system described in Example 1 was tested on two different EHCs with different hardness. The system functioned well with no changes to the system or software being needed for the different materials. HAMSTER is insensitive to the particular material.

The HAMSTER system described in Example 1 was used to identify bonded and debonded EHC on a variety of prepared kissing debonds, that is, debonds that leave extremely small gaps. In such cases, the deviation of the pulse from that of a bonded region occurs only briefly at the very beginning of the impact. It was found that lowering the trigger level (a data acquisition setting) for HAMSTER to enable less forceful swinging increased HAMSTER's sensitivity to the slighter deviation, leading to successful detection of such kissing debonds. HAMSTER was used to identify bonded and debonded EHC on several other vessels. As with the kissing debonds, the trigger level needed to be slightly adjusted for certain areas using certain EHCs.

Another HAMSTER system was constructed as described in Example 1, but the PCB model TLD086D20 sledge impulse hammer's force outputting force sensor was replaced with an accelerometer outputting force sensor, which output acceleration was then converted to force data by f=ma. This HAMSTER system was used successfully to identify bonded and debonded EHC on several vessels.

Example 3: HAMSTER Profile Building and Threshold Setting

The HAMSTER system as described in Example 1 was used to inspect two submarines in a variety of locations on their hulls, and with varying composition EHCs at such locations. The profile was constructed as follows:

Each force versus time pulse was analyzed separately. Each pulse was low pass filtered to minimize the effects of signal noise. Data above 10% of peak value were retained. The retained data were time warped such that the time basis was 0 to 1, that is, nondimensional time, t*. The time warped pulse was impulse normalized by dividing by the area under the trace. The resulting values are termed the normalized force, f*(t*). The normalized force pulse was subject to a nonlinear regression of Equation (7) and the parameters $p_1$ to $p_5$ were recorded.

$$f^*(t^*) = p_1 + p_2\sin(p_3 t^* + p_4)e^{-p_5 t^*} \tag{7}$$

When a pulse was a significant mismatch to this equation (for example, a false hit or major debond such as a flapper), the regression may fail and the trace would be excluded from further consideration. The normalized force pulse was reconstructed using the identified parameters and equation (1). The time-basis for this new pulse is 0 to 1 (nondimensional) in increments of 0.001. This pulse is termed F(t*). These pulses (one per measurement) are saved to use in the next step of the analysis.

The average profile P(t*) was calculated as the average of all the F(t*) reconstructed force pulses. The RMSD for each separate F(t*) was calculated using equation (8) where there are N=1001 time values in each pulse.

$$RMSD = \sqrt{\frac{\sum(F(t^*) - P(t^*))^2}{N}} \tag{8}$$

A histogram of the RMSD values (one per pulse) showed significant right skewness so the RMSD data was subjected to a square root function to form a more easily analyzed distribution.

The next step was to eliminate outliers. The Thompson-tau method was used, eliminating one outlier per iteration. After each outlier was eliminated, the process was repeated, with a revised profile being determined from the average of the remaining F(t*) pulses. The outlier elimination iteration was continued until there were no more identified outliers. At that point the remaining P(t*) profile was declared to be the final universal HAMSTER profile. A nonlinear regression of P(t*) yielded the five HAMSTER profile parameters. The HAMSTER threshold was declared to be the last RMSD peak value found during the outlier elimination iteration, which was consistent with a 99% confidence level.

For the two submarines examined, measurements were taken from two different regions, which regions presented different compositions of EHC. The results are shown below in Table 2, with all thresholds being calculated at a 99% confidence level:

TABLE 2

| Submarine 1 Region 1 410 measurements | Submarine 1 Region 2 360 measurements | Submarine 2 Region 1 925 measurements | Submarine 2 Region 2 160 measurements | All combined 1855 measurements |
|---|---|---|---|---|
| $p_1 = 0.7978$ | $p_1 = 0.7957$ | $p_1 = 0.7412$ | $p_1 = 0.7600$ | $p_1 = 0.7669$ |
| $p_2 = 0.8729$ | $p_2 = 0.8636$ | $p_2 = 0.9145$ | $p_2 = 0.9182$ | $p_2 = 0.8939$ |
| $p_3 = 4.9256$ | $p_3 = 4.9156$ | $p_3 = 4.6757$ | $p_3 = 4.7633$ | $p_3 = 4.7852$ |
| $p_4 = -0.8199$ | $p_4 = -0.8372$ | $p_4 = -0.7061$ | $p_4 = -0.7258$ | $p_4 = -0.7588$ |
| $p_5 = 0.1441$ | $p_5 = 0.1135$ | $p_5 = 0.1611$ | $p_5 = 0.1998$ | $p_5 = 0.1506$ |
| Threshold RMSD: 0.0417 | Threshold RMSD: 0.0265 | Threshold RMSD: 0.0357 | Threshold RMSD: 0.0395 | Threshold RMSD: 0.0411 |

Using the average from all the impacts, the recommended profile/threshold is found in the "All Combined" column. As more data is collected in the field, the profile/threshold can be further refined.

The HAMSTER profiles described above are based on the first cycle of a classic single degree of freedom vibration ring down, which has proven to be effective for identifying debonded EHC. However, in other embodiments of the invention and for other surface-material pairs, other mathematical profiles may be used. For example, one may use profiles based on excitation used in shock testing (such as half sine, haversine), or those based on different mathematical modelling (such as polynomial, coefficient of restitution). For EHC on submarine hulls, the ring down model outperformed these other potential profile shapes, although 6th order polynomial modeling appeared to be effective as well.

Example 4: Alternative HAMSTER Embodiments

HAMSTER Arrays

Inspecting the entire hull of a large vessel may be accomplished with a handheld HAMSTER device as exemplified in Example 1. Alternatively, the HAMSTER impulse hammer may be mounted on a frame or other stable structure, being retained in its ready position by, for example, a spring and a mechanical release mechanism, or other means known by those of skill in the art. In another alternative, instead of a traditional hammer form, the impulse hammer may be in the form of a piston with the force gauge head situate at the end thereof. Following release of the release mechanism, the impulse hammer impacts the EHC and supplies the resulting measured impulse data to the HAMSTER computer. The impulse hammer may then be returned to its ready position using means known in the art, such as another spring or a tether, operated by the user. In such an embodiment, the HAMSTER may be used at a greater distance from the hull than is possible with a handheld impulse hammer. For example, the frame structure bearing the impulse hammer may be positioned at the end of a longer member such as a pole. The operator extends the pole to place the mounted HAMSTER against a region of EHC coated hull. The force gauge is then triggered by the operator by mechanical means. In such embodiments, the force delivered at each impact is not subject to a particular operator's swing, but instead may be designed for repeatable, reliable impacts delivered with essentially the same degree of force.

The invention also contemplates using a plurality of such mounted non-handheld HAMSTERs simultaneously. An array frame structure is constructed with a plurality of HAMSTERs mounted thereon. The array is designed such that the pulse gauge heads may be triggered and operated remotely and/or automatically. The array frame structure may be built as a crawler that takes measurements from impacts of its pulse gauge heads, then crawls to an adjacent region and takes new impact data. Rather than communicating the results of each individual impact to the operator via LEDs, in these embodiments the HAMSTER system itself is equipped with means to mark the locations of debonded regions. For example, the array frame may be equipped with such marking means in the form of paint which is applied to debonded regions as they are identified. Alternatively, the HAMSTER system may be equipped with means of transmitting the data from all impacts to another computer capable of constructing a virtual map of the debonded regions, or a virtual map of the entire hull with bonded and debonded regions identified.

A HAMSTER was constructed in such fashion using a modified HAMSTER hammer of Example 1, and using an accelerometer as the force sensor as described in Example 2. An air cylinder provides easy air pressure adjustments enabling control of the impact force of the hammer head. Air pressure is also readily available in shipyards. As the head of the hammer was screwed to the shaft, the head featured a female thread. The shaft was removed and the head of the hammer was threaded onto a double acting air cylinder shaft rod having a male thread. The hammer head and air cylinder assembly was mounted on a crawler capable of attachment to and crawling on an EHC coated ship hull. The assembly can be mounted on any such crawler type structure, for example, an frame constructed of ordinary 80/20 T-slot aluminum. To minimize the weight mounted on the crawler, a cable length of 50-100 feet was provided between the HAMSTER on the hull crawler and the HAMSTER electronics housing box. A second cable length was provided from the air cylinder portion of the assembly to the box controlling the air cylinder, thereby allowing triggering of the impacts, control of air pressure (and thus the force applied), and the timing of impacts.

The crawler was mounted on the hull, and the controller initiated the crawling process. As the crawler crawled, the air cylinder fired, resulting in an impact by the HAMSTER hammer head. The crawler crawled to another region, repeating impacts and collection of data over several regions. The process was thus automated. The HAMSTER functioned essentially the same as a handheld HAMSTER, producing results indicating bonded and debonded regions. Multiple air cylinder mounted HAMSTER assemblies may be mounted to such crawlers, allowing for multiple regions to be assessed for bonding and debonding simultaneously, followed by crawling and obtaining additional measurements at additional locations. The process can thus be used to examine the entirety of a hull. The assemblies may also be provided with marking devices, such as spray paint, to indicate areas of bonding or debonding.

Aquatic HAMSTER

The HAMSTER system may be waterproofed in order to conduct inspection and detection of the underwater hull portions of a ship afloat, rather than in dry dock. While different characteristics of pulse curves may emerge under water, the HAMSTER profile is built in the same manner as provided herein. The trigger values, the necessary initial impact forces, and other elements are adjusted to suit water-based impacts. Additionally, the pulse duration may be adjusted from its usual 10%-10% for operation in air to the optimal duration for underwater analysis, based on routine experimentation. A HAMSTER profile and threshold may thus be developed which are effective at identifying bonded and debonded EHC at underwater locations.

HAMSTER for Aircraft

Aircraft may have laminates bonded to their bodies' external structural substrate to provide a variety of advantages, from corrosion resistance to aerodynamics to reducing visibility to radar. HAMSTER is equally adept at, and adaptable to, detecting debonding of such laminate from the structural substrate. Using the devices and methods provided herein, a HAMSTER profile is constructed and applied to detecting such debonding in a rapid, efficient, and accurate manner.

HAMSTER for Other Structures

Nonmetal structures, such as composites, may have laminates bonded thereto to provide a variety of advantages which would be partially or wholly lost in the case of debonding lamination in regions thereof. HAMSTER is equally adept at, and adaptable to, detecting debonding of such laminate from the structural substrate. Using the devices and methods provided herein, a HAMSTER profile is constructed and applied to detecting such debonding in a rapid, efficient, and accurate manner.

Other laminate structures include composite structures of two layers of equal or different thicknesses, sandwiches of three or more layers of varying thickness, and the like. The thickness of such laminates may vary from thinner coatings or layers less than one quarter of an inch thick to thicker coatings or layers greater than four inches thick. HAMSTER is equally adept at, and adaptable to, detecting debonding between the layers of such laminate structures. Using the devices and methods provided herein, a HAMSTER profile is constructed and applied to detecting such debonding in a rapid, efficient, and accurate manner.

The present invention is not to be limited in scope by the specific embodiments described above, which are intended as illustrations of aspects of the invention. Functionally equivalent methods and components are within the scope of the invention. Various modifications of the invention, in addition to those shown and described herein, will be readily apparent to those skilled in the art from the foregoing description. Such modifications are intended to fall within the scope of the appended claims. All cited documents are incorporated by reference as if fully set forth herein.

What is claimed is:

1. A device for detecting a bonded state or a debonded state between layers of a laminate structure, the device comprising:
   an impulse hammer comprising a hammer head comprising a force sensor; and
   a computer having programmed therein a universal profile and a profile threshold;
   wherein, when the impulse hammer impacts a region of the laminate for a time period, the force sensor delivers force versus time pulse data to the computer, the force versus time pulse data comprising a plurality of data points spanning fractions of the time period;
   the computer normalizes the pulse data to yield a normalized pulse curve, compares the normalized pulse curve to the universal profile, and calculates a root mean square difference (RMSD) between the normalized pulse curve and the universal profile; and
   if the RMSD exceeds the profile threshold, the computer provides a notification that the laminate is in a debonded state.

2. The device of claim 1, further comprising:
   if the RMSD does not exceed the profile threshold, the computer provides a notification that the laminate is in a bonded state.

3. The device of claim 1, further comprising an enclosure to house the computer, the computer being attached by a cord to the impulse hammer.

4. The device of claim 3, further comprising a battery pack and a signal conditioner housed within the enclosure, and wherein the enclosure has means for being worn by an operator.

5. The device of claim 1, wherein the impulse hammer houses the computer, a battery pack, and a signal conditioner.

6. The device of claim 1, wherein the laminate structure is a substrate-laminate selected from the group consisting of a submarine hull, a surface ship hull, and an aircraft body.

7. The device of claim 1, wherein the force sensor directly measures force and outputs force data.

8. The device of claim 1, wherein the force sensor is an accelerometer which directly measures acceleration and outputs acceleration data which may be converted to force data.

9. The device of claim 1, wherein the impulse hammer's impulse hammer head is mounted on an air cylinder, the air cylinder being controlled by an air cylinder controller capable of triggering an impact of the impulse hammer head against a laminate structure.

10. An apparatus comprising a plurality of devices of claim 9, wherein the impulse hammers form an array, each impulse hammer in the array delivers pulse data from impact to the computer, and for each pulse data the computer determines a bonded state or a debonded state.

11. The apparatus of claim 10 further comprising means to crawl to at least one additional location after the array has measured impacts at a first location, and optionally further comprising a means of marking debonded regions with visible markings.

12. A method for determining a bonded state or a debonded state between layers of laminate structure, the method comprising the steps of:
   impacting a region of the laminate structure with a device of claim 1;
   receiving the force versus time pulse data from the pulse hammer;
   normalizing the pulse data to produce a normalized pulse curve; and
   calculating a pulse RMSD by comparing the normalized pulse curve to a universal profile;
   whereby, if the pulse RMSD exceeds a profile threshold, the laminate structure is determined to be in a debonded state, and if the pulse RMSD does not exceed the profile threshold, the laminate structure is determined to be in a bonded state.

13. The method of claim 12, wherein the pulse RMSD is calculated according to $$RMSD = \sqrt{\frac{\sum (f^*(t^*) - P(t^*))^2}{N}}$$

wherein f* is a nondimensional force, t* is a nondimensional time, f*(t*) is the normalized pulse curve, P(t*) is the universal profile, and N is a number of time points in the pulse data.

14. The method of claim 12, wherein the universal profile is generated by the steps of:

subjecting a plurality of normalized pulse curves to a mathematical regression to establish a plurality of parameters parametrically describing each of the normalized pulse curves;

averaging each of the parameters to produce a working profile;

comparing each normalized pulse curve to the working profile to produce an RMSD for each normalized pulse curve;

generating a working profile histogram comprising the RMSDs;

iteratively eliminating outlier pulse RMSDs to refine the working profile histogram until a confidence level is reached;

wherein the last refined working profile is deemed to be the universal profile.

15. The method of claim 14, wherein the mathematical regression is regression selected from the group consisting of a nonlinear regression and a linear regression.

16. The method of claim 15, wherein the nonlinear regression is performed according to $$f^*(t^*) = p_1 + p_2 \sin(p_3 t^* + p_4) e^{-p_5 t^*}$$

wherein f* is a nondimensional force, t* is a nondimensional time, $p_1$ is a DC offset to long-term equilibrium position, $p_2$ is a mean-to-peak amplitude, $p_3$ is a ring-down frequency, $p_4$ is a phase, and $p_5$ is an energy dissipation term calculated as a product of a viscous damping ratio and a natural frequency.

17. The method of claim 14, wherein the RMSD is calculated according to $$RMSD = \sqrt{\frac{\sum (f^*(t^*) - p(t^*))^2}{N}}$$

wherein f* is a nondimensional force, t* is a nondimensional time, f*(t*) is the normalized pulse curve, p(t*) is the working profile, and N is a number of time points in the pulse data.

18. The method of claim 12, wherein the laminate structure is a substrate-laminate selected from the group consisting of a submarine hull, a surface ship hull, and an aircraft body.

19. The method of claim 18, wherein a plurality of devices are mounted in an array; each impulse hammer's impulse hammer head is mounted on an air cylinder; the air cylinders are controlled by an air cylinder controller capable of triggering an impact of the impulse hammer head against a laminate structure; and the method further comprises the step of triggering a plurality of impacts at more than one location of the laminate structure, whereby the bonded or debonded state is determined.

20. The method of claim 19, further comprising the step of applying a marking at locations identified as debonded.

* * * * *